United States Patent [19]

Ahlstrom, Jr. et al.

[11] 4,359,891
[45] Nov. 23, 1982

[54] REPETITIVE CHROMATOGRAPHIC APPARATUS

[75] Inventors: Ross C. Ahlstrom, Jr.; Mark S. Johnson, both of Lake Jackson; Jerry P. Moore, Katy; Ivo R. Schoppe, Jr., Lake Jackson, all of Tex.

[73] Assignee: The Dow Chemical Company, Midland, Mich.

[21] Appl. No.: 222,419

[22] Filed: Jan. 5, 1981

[51] Int. Cl.³ .................... G01N 31/08; B01D 15/08
[52] U.S. Cl. ........................................ 73/23.1; 422/89
[58] Field of Search .................... 73/23.1, 61.1 C; 422/70, 89

[56] References Cited

U.S. PATENT DOCUMENTS

| 2,757,541 | 8/1956 | Watson et al. | 73/422 |
| 2,830,738 | 4/1958 | Sorg et al. | 222/133 |
| 2,972,888 | 2/1961 | Lamkin | 73/422 |
| 2,981,092 | 4/1961 | Marks | 73/23 |
| 3,126,732 | 3/1964 | Sanford | 73/23 |
| 3,236,603 | 2/1966 | Durrett et al. | 73/23.1 |
| 3,263,493 | 8/1966 | Davidson | 73/23.1 |
| 3,267,736 | 8/1966 | Boettger | 73/422 |
| 3,394,582 | 7/1968 | Munro | 73/23.1 |
| 3,475,950 | 10/1969 | Ferrin | 73/23.1 |
| 3,518,059 | 6/1970 | Levy | 73/23.1 |
| 3,859,209 | 1/1975 | Jahnsen et al. | 73/23.1 |
| 3,916,465 | 10/1975 | Jones | 73/23.1 |
| 4,007,626 | 8/1976 | Roof et al. | 73/23.1 |
| 4,151,741 | 5/1979 | Schirrmeister | 73/23.1 |
| 4,287,752 | 9/1981 | Ury | 73/23.1 |

OTHER PUBLICATIONS

Journal of Gas Chromatograph by O. L. Hollis and W. B. Hayes, vol. 4, No. 7, pp. 235–239, Jul. 1966.

Primary Examiner—Howard A. Birmiel
Attorney, Agent, or Firm—M. W. Barrow

[57] ABSTRACT

A repetitive gas chromatograph employing a backflush valve downstream from the detector and a separate sample injection valve located upstream located directly upstream from the single chromatographic column. Each valve is operated independently of the other so as to allow flexibility in the timing of going into backflush operation and returning the sample valve immediately after sample injection onto the column to sample passage through the sample valve so as to more quickly establish equilibration of the sample and the sample valve's walls. Type and location of sample valve and backflush valve allow continuous monitoring of a sample stream.

4 Claims, 6 Drawing Figures

REPETITIVE CHROMATOGRAPHIC APPARATUS

BACKGROUND OF THE INVENTION

This invention relates to gas chromatography. More particularly, it relates to an arrangement of a sampling valve and a backflush valve which are capable of being operated independently of one another as well as relating to two temperature control zones, all of which cooperate with a single chromatographic column and a detector means to provide the capability for very accurate, rapid, on-line analysis of process streams, particularly organic process streams containing trace amounts of water and chlorine or hydrogen chloride.

In general, gas chromatography is an analytical technique widely used for the qualitative and quantitative analysis of liquid and gaseous mixtures. In recent years this technique has become increasingly important in determining components present in a sample to be analyzed. In general, a sample of a mixture is obtained from a stream to be analyzed and passed through one or more columns wherein the components are separated and then separately passed to a detector which measures the separated components of the mixture in order of their elution times. Columns may be then backflushed to remove any retained components from the column.

It is known to provide means such as a sampling valve wherein a small sample of a liquid or a gaseous mixture is measured and then carried into the column by means of a carrier gas, in which column the components of the mixture are separated and gradually eluted from the column into the detector means. In the chromatographic analysis of a sample containing both easily and difficultly eluted components, the more rapidly eluted component is separated and passed into the detector well before the more difficultly eluted component leaves the chromatographic column. When this type of analysis is being run, it is known practice to backflush the chromatographic column with a stream of carrier gas or a suitable flushing gas to remove the retained components through the inlet end of the chromatographic column. Backflushing of this type frees the column for another analysis. Suitable valving and lines must be supplied in addition to the basic apparatus to permit this backflushing.

In many chromatographic analyses two or more chromatographic columns are connected in series. It is also known to provide one or more valves programming the several carrier and backflushing gas streams as well as sample streams to efficiently operate the chromatographic analysis. Such arrangements as are presently known, involving several columns and/or several valves, are time consuming and add to the equipment and maintenance costs.

It is further known to use a single programming valve which performs simultaneous sampling and backflushing in a gas chromatographic system containing a single chromatographic column and detector; said column and detector being connected directly together to avoid dead space between them. See Jones, A. W., "Multi-Stream Gas Chromatographic Method and Apparatus", U.S. Pat. No. 3,916,465, issued Nov. 4, 1975.

There are many things known about making gas chromatographic analyzers. Nevertheless maintaining the accuracy of gas chromatographic devices, while making them sufficiently reliable to be placed in on-line process stream monitoring duty has not been achieved while also giving them the ability to immediately switch into a backflush mode once the component of the stream being monitored is detected and further giving such device sufficient flexibility to be adjusted for different stream component analysis, that is adjusted as to time of sample injection at time and length of backflushing.

It would be advantageous to have a gas chromatographic analyzer and method which is simple yet which is capable of rapid, repetitive gas chromatographic analysis of process streams with greater accuracy, durability, and flexibility than heretofore available. These advantages are found in the present invention.

SUMMARY OF THE INVENTION

This invention is an improved apparatus and method for gas chromatographic analysis. The following elements are known elements used in gas chromatography: (a) a chromatographic column having a sample inlet and sample outlet, and containing a column packing suitable for separating at least one component of a product desired to be monitored; (b) a detector also having a sample inlet and sample outlet; (c) a reference cell associated with said detector having a reference gas inlet and a reference gas outlet; (d) a carrier gas supply and if desired a reference gas supply which may be different from the carrier gas; (e) a carrier gas vent; (f) a backflush valve; (g) a sample valve; (h) a pressure regulating means; (i) a temperature regulating means; and (j) a valve switching means.

The improvement of this invention provides for a gas chromatographic analysis system which is capable of rapid, repetitive, on-line analysis of liquid process streams, particularly for on-line analysis for trace amounts (about 2–500 ppm) of water in organic streams containing hydrogen chloride or chlorine. As is known even trace amounts of water in such chlorine containing streams causes extensive monetary loss each year due to vastly increased hydrochloric acid corrosion of such metal parts as reactors, heat exchangers, pipeline and the like.

The improved apparatus of this invention comprises the following combination:

(1) a single chromatographic column having a sample inlet and a sample outlet and containing a suitable column packing material;

(2) a detector in direct fluid communication with the chromatographic column at the column's outlet by having the detector's sample inlet closely abutting (preferably directly abutting), the column's outlet;

(3) a backflush valve which is capable of being switched to different flow positions and having at least four ports and at least two channels (or chambers) which are moveable with respect to these ports in a manner such that each channel is capable of forming a fluid communication link between separate pairs of the ports of the backflush valve; this backflush valve being in fluid communication via its first port with the detector through the detector's sample outlet, this backflush valve being in fluid communication via its second port with a vent, and this backflush valve being in fluid communication via its third port with a carrier gas supply source;

(4) a sample valve which is capable of being switched to different flow positions independently of the switching of the backflush valve; said sample valve having at least four ports and at least a first, second, and third channel, the channels being moveable with respect to the sample valve's ports in a manner such that each channel is capable of forming a fluid communication link between a pair of the sample valve's four ports according to the position to which the sample valve is switched; said sample valve being in direct fluid communication via its first port with the inlet of the chromatographic column by having said inlet at least closely abutting (preferably directly abutting) the first port of the sample valve; said sample valve being in fluid communication via its second port with the backflush valve through the fourth port of the backflush valve; said sample valve capable of being in fluid communication via its third port with a process stream to be analyzed, and said sample valve being in fluid communication via its fourth port with an exit for the sample, said exit preferably being capable of leading back to the process stream, but not necessarily so;

(5) a pressure regulating means capable of maintaining carrier gas flowing into the sample valve via its second port from the fourth port of said backflush valve at a substantially lower pressure than the sample when flowing from the first port of said sample valve into the inlet of said column;

(6) a first temperature regulating means associated with the sample valve for controlling the temperature of any sample flowing through the sample valve from a process stream to be analyzed;

(7) a second temperature regulating means for controlling the temperature of the carrier gas, the chromatographic column, the detector and the reference cell at a predetermined, constant temperature; and (8) a valve switching means capable of independently switching the backflush and sample valves to their two different flow positions (defined below) manually, but preferably automatically by a programmed cyclic control unit.

The first flow position of the backflush valve is one in which one of its channels forms a fluid communication link between its first port and its second port while another of its flow channels forms a fluid communication link between its third and fourth ports. The second flow position of the backflush valve is one in which one of its flow channels forms a fluid communication link between its first and third ports while another of its channels forms a fluid communication link between its second and fourth ports.

The first flow position of the sample valve is one in which the first of its channels forms a fluid communication link between its first and second ports while its second channel forms a fluid communication link between its third and fourth ports. The second flow position of the sample valve is one in which its second channel forms a fluid communication link between its first and second ports while its third channel permits a liquid communication link between its third and fourth ports. This second position of the sample valve allows a constant volume of liquid sample to be injected into the chromatograph column each time the sample valve is switched from its first position to its second position. Injections of constant volumes of liquid sample is critical to obtaining accurate readings of the concentration trends with respect to time of the stream being monitored. Constant volume is assured because the same sample valve channel, its second channel, is used each time sample is injected onto the column, for this second channel traps the exact same volume within it each time the sample valve is switched from its first position to its second position.

When the sample valve is in its second position, its third channel allows sample to continue to run through the sample valve which allows the sample valve to remain at a more constant temperature. This too is one of the features which improves the accuracy of the chromatographic analysis system.

Finally, it should be emphasized that the pressure regulating means is coordinated with the first and second temperature regulating means so that liquid sample flowing in the sample valve from its third port to its fourth port through its second channel will remain liquid therein but has sufficient energy contained in the liquid so that it will immediately volatilize upon sample valve's switching to its second position wherein the sample trapped in the sample valve's second channel is suddenly injected into the carrier gas between the sample valve's first and second ports.

The present invention also includes a method of operating a gas chromatographic analyzer to give improved accuracy and faster results for repetitive monitoring of a product. An example of such monitoring is the repetitive, rapid, on-line monitoring of chemical streams such as the monitoring of chlorinated organic production streams for water content.

A better understanding of the invention may be had by reference to the drawings wherein like elements have the same reference number.

DETAILED DESCRIPTION OF THE PREFERRED EMBODIMENT

Figure 1:
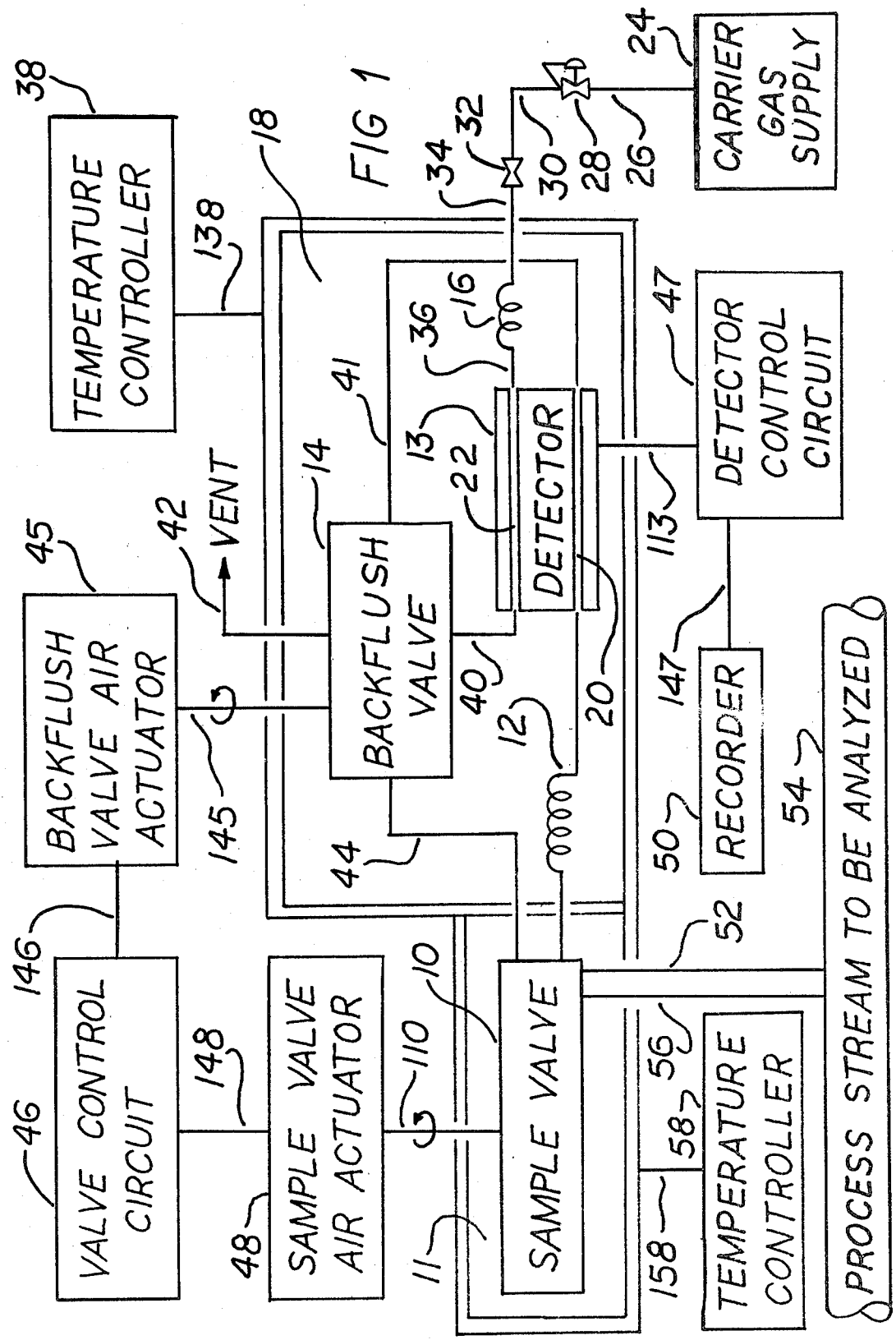
FIG. 1 is a schematic diagram of the present invention.

Referring to FIG. 1, a diagrammatic sketch of the apparatus of this invention can be seen which particularly demonstrates that two separate temperature zones 11, 18 are employed. The temperature of sample valve 10 is controlled by one temperature control zone 11. Analytical (gas chromatograph) column 12, detector 13, backflush valve 14, and carrier gas pre-heat coil 16 are shown controlled by enclosure in a second temperature control zone 18. Preferably this second temperature control zone 18 is an oven air bath. The purpose of having these two different temperature control zones was given above and will be discussed further below.

Also seen to be employed are two independent valves, sample valve 10 and backflush valve 14, with backflush valve 14 located outside the flowpath formed between sample valve 10, column 12, and detector 13. Further employed is a pressure regulating means, shown here as pressure regulating valve 28, for maintaining a predetermined pressure difference between sample flowing through sample valve 10 from line 52 and carrier gas flowing into the inlet of column 12 through sample valve 10.

The inlet of the gas chromatographic column 12 is in direct fluid communication with sample injection (or sample introduction) valve 10 so that a sample from valve 10 can be injected directly onto the gas chromatographic column packing contained in chromatograph column 12 to thereby minimize dead space between the sample injection point and the column packing. This direct injection is achieved by having the inlet closely abutting, preferably directly abutting, sample valve 10. The elimination of this dead space minimizes the surface area of tubing between sample injection point and column packing. Such surface area absorbs water and therefore distorts the true water concentration content of the organic stream. Additionally the elimination of this dead space minimizes the dispersion of the sample in the carrier gas before it contacts the column packing. This gives the sharper peak resolution which is particularly desireable for gas chromatographic analysis. For the same reasons the outlet of the gas chromatographic column 12 is in direct fluid communication with the inlet of detector 13 by having the column outlet closely abutting, preferably directly abutting, the inlet of detector 13.

Detector 13 has two separate gas passageways through it, one referred to as the "sample gas passage" 20 and the other referred to as the "pure carrier gas passageway" 22 (or "reference gas passageway" 22). Detector 13 has a sample inlet and sample outlet at the ends of sample gas passageway 20. Associated with detector 13 is a reference cell which is represented in FIG. 1 merely by reference gas passageway 22 contained in detector 13. Passageway 22 is shown with its entrance for reference gas and its exit. It is known by those skilled in the art that such reference cells are necessary to make accurate gas chromatographic analysis. It is also known that the reference gas need not be the same as the carrier gas; however, it is most convenient to do so in this invention. This invention does not require that the carrier gas flowing from line 36 to backflush valve 14 via line 40 pass through reference passageway 22 as shown, although it is simpler to do so. Rather the carrier gas could bypass reference passageway 22 and flow directly from line 36 around reference passageway 22 straight into backflush valve 14 with other provision made for supply of reference gas to reference 22.

A carrier gas source 24 provides a carrier gas such as helium, nitrogen or other gases suitable as a carrier gas for use with a gas chromatographic column. Carrier gas flows from carrier gas supply 24 via line 26, through pressure regulating valve 28, through line 30, through flow controller 32, through line 34, through carrier gas pre-heat coil 16, through line 36 into the pure carrier gas passageway 22 of detector 13.

Valve 28 maintains the flowing carrier gas at a constant pre-determined pressure. Flow controller 32 maintains the flowing carrier gas at a constant, pre-determined flowrate. Pre-heat coil 16 elevates the temperature of the carrier gas in accordance to the pre-determined temperature setting of oven air bath's 18 temperature. The temperature of oven air bath 18 is maintained at a constant, pre-determined temperature by temperature controller 38. Temperature controller 38 is thermally linked to oven 18 by thermal linkage means 138.

By passing the carrier gas through pressure regulating valve 28, flow controller 32, and carrier gas pre-heat coil 16, the carrier gas arrives at, and flows through, carrier gas passageway 22 at a constant pressure, flowrate, and temperature. Thus the carrier gas flowing through carrier gas passageway 22 provides a very uniform standard against which unknown gases flowing through sample gas passageway 20 of detector 13 can be compared and measured by detector-control 47 and recorded by recorder 50. Determining this temperature and pressure will be discussed below.

Note, in passing, however, that pressure regulating valve 28 and flow controller 32 could both be installed in other locations. For example, they could be installed in line 44, or either one could be left where it is and the other installed in line 44. Their location is not critical except that they be on the upstream side of sample valve 10. This upstream side is defined as the upstream side of the column inlet when gas is flowing from line 44 through sample valve 10 into column 12.

In this preferred embodiment, the outlet of pure gas passageway 22 of detector 13 is maintained in constant fluid communication with backflush valve 14 via line 40 so that the carrier gas continually flows through passageway 22 to backflush valve 14.

Backflush valve 14 is maintained in fluid communication with the outlet of sample gas passageway 20 of detector 13 via line 41; it is maintained in fluid communication with a vent 42 out of the system; and it is maintained in fluid communication with sample injection valve 10 via line 44. Backflush valve 14 is preferably a rotatable two channel, four port, two-position valve. Such valves are commercially available from Valco Instrument, Co. of Houston, Tex. Backflush valve 14 is capable of being rotated at pre-set times by backflush valve air actuator 45 through mechanical linkage 145. Actuator 45 is actuated by automatic valve control circuit means 46 through electrical linkage 146. Backflush valve 14 contains at least two flow channels (not shown in FIG. 1, but see FIGS. 2, 4, 5, 6 and further discussion below). These two flow channels are not in fluid communication with one another. Backflush valve 14 has two flow positions, in which it is operated, a first or forward flow position and a second or backflush flow position. These two flow channels, four ports, and the port connections to the rest of the system of backflush valve 14 can be more easily seen by reference to FIG. 2. The two different positions of backflush valve 14 will be discussed in FIGS. 4, 5 and 6.

Figure 2:
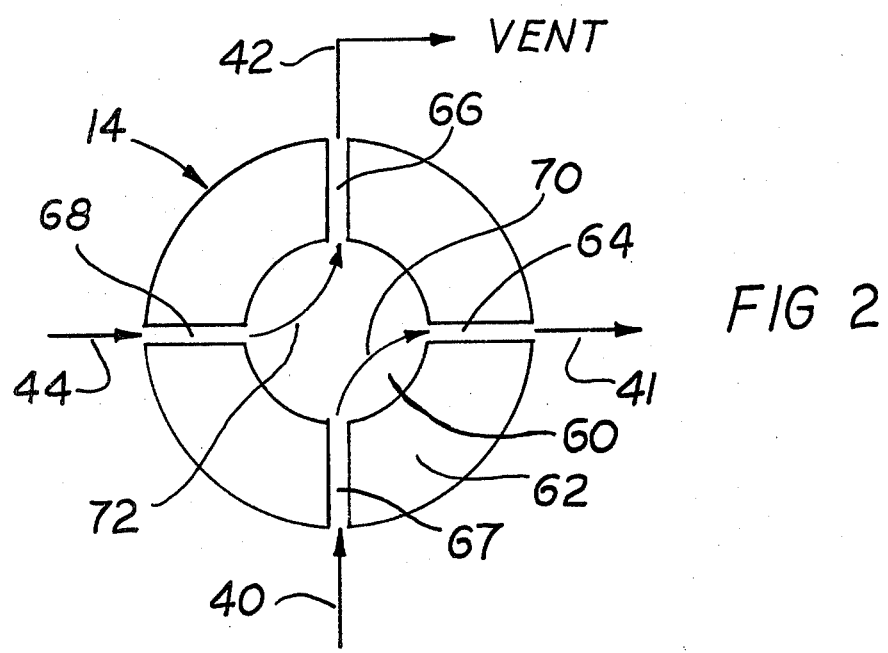
FIG. 2 is a schematic view of one embodiment of the backflush valve of the system.

Referring to FIG. 2, backflush valve 14 can be more easily seen. It is shown in one of its two necessary flow positions, in this instance its "second" or "backflush flow" positions. Backflush valve 14 has an inner ring 60 and an outer ring 62. Inner ring 60 is rotatable within outer ring 62. Outer ring 62 has four ports located in it for passage of fluid. Backflush valve's first port 64 is connected to and in fluid communication with line 41; its second port 66 is connected to and in fluid communication with vent line 42; its third port 67 is connected to and in fluid communication with line 40; and its fourth port 68 is connected to and in fluid communication with line 44.

Backflush valve's inner ring 60 contains two flow channels 70 and 72 to provide fluid communication inside backflush valve 14 between its ports 64, 66, 67 and 68 taken in pairs. Internal ring 60 is rotatable within external ring 62 so that flow channels 70, 72 can form a fluid communicating link with different pairs of ports 64, 66, 67 and 68. In FIG. 2 flow channel 70 is shown forming a fluid communication link between port 64 and port 67 while flow channel 72 is shown forming a fluid communication link between ports 68 and 66. This flow position conforms to the "second flow position" defined above in the Summary of the Invention. The configuration of backflush valve 14 which would conform to the backflush valve's "first flow position", also defined above, is the configuration where inner ring 60 is rotated such that one flow channel, say flow channel 70 for example, forms a fluid communication link between port 66 and 64 while the other flow channel 72 forms a fluid communication link between ports 67 and 68. This second flow position of backflush valve 14 can be seen in FIG. 4.

The sample valve 10 is preferably a conventional rotary liquid sample valve. Such valves are commercially available in modified form from Valco Instrument, Co. of Houston, Tex. Referring back to FIG. 1, it can be seen that a sample stream is fed by line 52 from the process stream to be analyzed 54 to and through valve 10. A line 56 is provided for return of the process sample stream from sample injection valve 10, or for flowing it to other places such as to waste. By referring to FIG. 3, a better understanding can be had with respect to sample injection valve 10. Therein it can be seen that sample valve 10 is much like backflush valve 14. But again, however, it should be emphasized that these two valves are operated independently of one another; i.e., the change of one does not automatically force a change in the other at the same time. These valves independence of each other gives a flexibility of operation not heretofor obtainable with an automatically operated, repetitive gas chromatograph.

Two differences which are immediately visible are sample valve 10 has three flow channels instead of two, and it is connected to different lines except for line 44. Sample valve 10 is described as a rotatable, four port, three channel valve.

Figure 3:
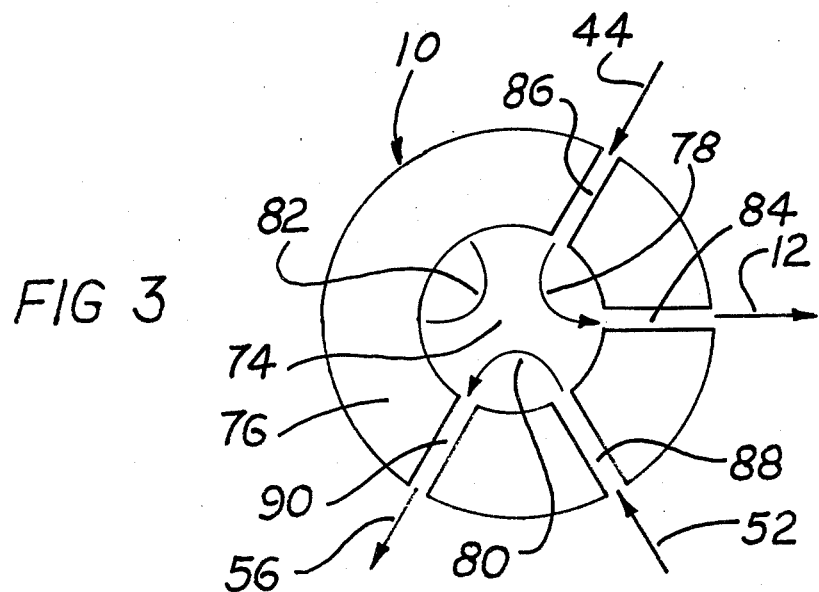
FIG. 3 is a schematic view of one embodiment of the sample injection valve of the system.

In FIG. 3, backflush valve 10 can be seen to have an inner ring 74 which is rotatable within an outer ring 76. Inner ring 74 contains first flow channel 78, second flow channel 80 and third flow channel 82. Outer ring 76 contains first port 84, second port 86, third port 88, and fourth port 90. In FIG. 3, sample valve 10 is shown: with flow channel 78 forming a fluid communication link between port 84 and port 86; with flow channel 80 forming a fluid communication link between port 88 and port 90; and with flow channel 82 resting in an idle position within the valve. This configuration of the ports and flow channels of sample valve 10 conforms to the definition of the sample valve's "first flow position" given above in the Summary of the Invention. This first flow position can be seen also in FIGS. 4 and 6. The second flow position can be seen in FIG. 5 wherein channel 80 has been rotated from forming a fluid communication link between ports 88 and 90 to a position wherein it forms a fluid communication link between ports 84 and 86. In this rotation to the second flow position, channel 82 is located such that it forms a fluid communication link between ports 88 and 90.

Returning to FIG. 1, the sample injection valve 10 is rotated into its second flow position by a valve switching means such as sample valve air actuator 48. Actuator 48 rotates valve 10 via mechanical linkage 110. Actuator 48 is controlled by automatic valve control circuit 46 through electrical linkage 148.

The pressure of the sample stream 54 is usually allowed to be whatever pressure is available from the process stream although this pressure could also be increased or decreased by known pressure changing devices. The temperature of the liquid sample stream flowing through sample injection valve 10 is adjusted to a pre-determined temperature by a temperature control means 58. Temperature controller 58 is in thermal communication with temperature control zone 11 via thermal linkage 158.

The relationship between the temperature and pressure of the sample stream flowing in the sample injection valve 10 to the temperature and pressure of the carrier gas is determined as follows. The temperature and pressure of the sample stream must be such that the sample stream remains a liquid when it is flowing through the sample injection valve 10 when the valve is in its "first flow position" or "carrier gas operational configuration", that is when the sample stream is not exposed to the carrier gas while it is being introduced into the column. However, the temperature and pressure of the liquid sample stream flowing in the sample injection valve must be such that this liquid sample will instantly volatilize upon exposure to the temperature and pressure at which the carrier gas is maintained.

Continuing with the discussion of the preferred embodiment of FIG. 1, the outlet of chromatograph column 12 is connected directly to and is in direct fluid communication with sample gas passageway 20 of detector 13 to eliminate error-introducing dead space between the column 12 and the detector 13.

The detector 13 can be any detector capable of detecting trace amounts of water in organic streams containing chlorine and/or hydrogen chloride. The preferred type detector is a thermal conductivity detector. Such detectors are available from Gow-Mac Instrument, Co. of Madison, N.J.

Electrically connected via electrical linkage 113 to detector 13 is a detector control circuit 47. Its function is to process the signal from detector 13 and provide necessary zero and span capabilities. Connected via electrical linkage 147 to detector control circuit 47 is a recorder 50 for recording the water concentration analysis data of the total detector-chromatographic column system.

The column packing inside column 12 is chosen for the desired elution. However, the column packing contained in chromatographic column 12 is very important for trace amounts of water, as is its preparation.

Figure 4:
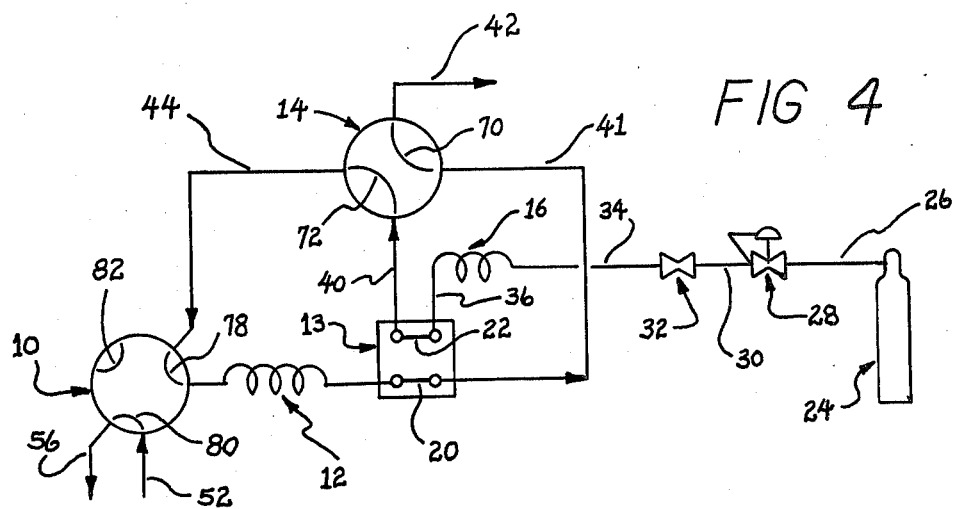
FIGS. 4, 5 and 6 are flow diagrams for the present invention showing various valve positioning with accompanying varying stream flowpaths, omitting the two separate temperature zones and other non-flow directional elements.
Figure 5:
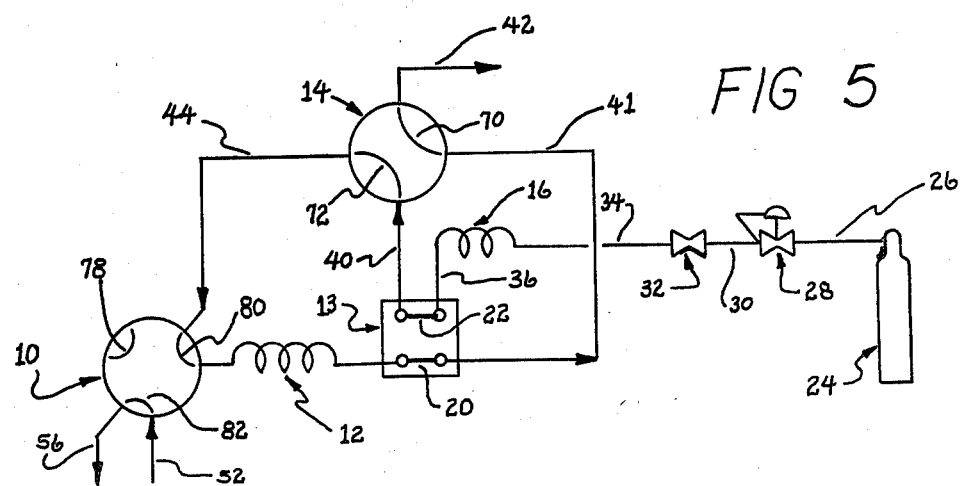
Figure 6:
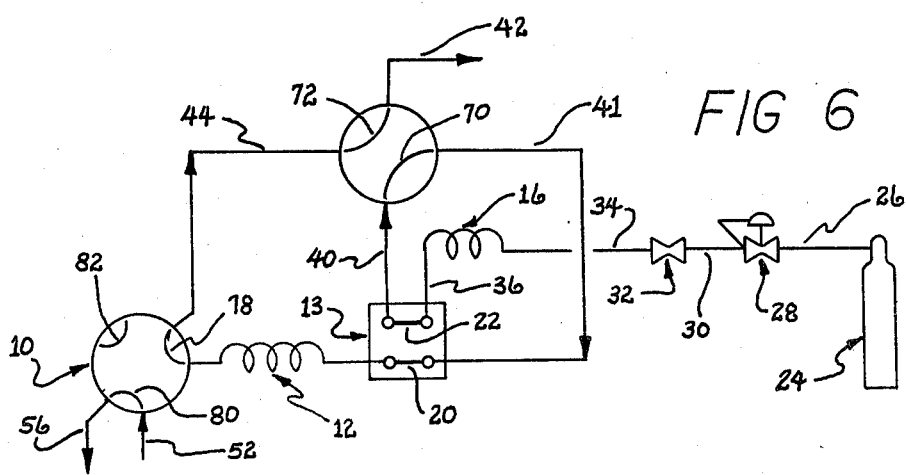

The method of operation of this invention can best be understood by reference to FIGS. 4, 5 and 6. The elements of these three Figures are the same and have reference numbers corresponding to those in FIGS. 1 and 2. In fact, because of the great similarity of FIGS. 4, 5, 6, only FIG. 4 will be fully numbered with FIGS. 5 and 6 only having reference numbers deemed appropriate to a better understanding of the invention. Note, however, that not all elements of this embodiment are shown in FIGS. 4, 5 and 6. Note particularly that the two temperature control zones are not shown and that the ports of the valves 10, 14 are not shown.

In FIG. 4 carrier gas, preferably helium, is continually flowed from carrier gas supply 24 through line 26, through pressure regulating valve 28, through line 30, through flow controller 32, through line 34, through carrier gas pre-heat coil 16, through line 36, through pure carrier gas passageway 22 of detector 13, and on through line 40 to backflush valve 14. The carrier gas follows this flowpath throughout all other configurations of valves 10 and 14 as shown in FIGS. 5 and 6. The flow is at a constant temperature, pressure, and flowrate throughout all configurations, except, of course, for the momentary instances when this carrier gas flowrate is stopped as valves 10 and 14 are switched from one operating configuration to another. Hence this description of the flow of the carrier gas from source 24 to valve 14 need not be repeated when the different flow configurations of FIGS. 5 and 6 are discussed.

Returning to FIG. 4, the carrier gas continues its flow through backflush valve 14 by way of channel 72, on through line 44, through sample injection valve 10 via carrier gas flow channel 78, through column 12, through sample gas passageway 20 of detector 13, through line 41, through backflush valve 14 by way of channel 70, and onto vent via line 42. The configuration of backflush valve 14 here described is what is defined above as the "first flow position" or the "forward flow configuration" of the backflush valve.

Meanwhile, while still referring to FIG. 4, attention is directed to the configuration of the sample injection valve 10. Besides having carrier gas flowing through sample valve 10 via carrier gas flow channel 78, liquid sample stream is continuously flowing into sample flow channel 80 of sample valve 10 from line 52. This sample stream leaves flow channel 80 via line 56. This continuous flow is continued until the sample has achieved the desired temperature and the walls of flow channel 82 have stopped absorbing any water from the sample. This is a critical occurrence, but the length of time is takes can only be determined by trial and error for any given valve and any given flow stream. When the sample valve is in the immediately above defined mode of operation, it is in what is referred to as its "first flow position" or its "carrier gas operational configuration". Before leaving FIG. 4, it must be pointed out that the flow of the carrier gas through the column 12 and detector 13 must be for a time sufficient to allow the column and detector to stabilize. The time it takes to accomplish this must be established by trial and error for each different organic stream.

Referring now to FIG. 5, it can be seen that backflush valve 14 has remained in its "first flow position", but sample injection valve 10 has been switched from its first flow position to its second flow position. That is, sample injection valve 10 has now been switched so that its sample flow channel 80 is now the fluid communication link between chromatograph column 12 and line 44. This switching is carried out automatically at pre-set times by valve control circuit 46 and air actuator 48 (FIG. 1). Also note particularly that when sample valve 10 is switched from the configuration shown in FIG. 4 to that shown in FIG. 5, it carries inside channel 80 a specific, fixed volume of liquid sample into the flowpath of the carrier gas flowing into chromatograph column 12 from line 44. Because of the temperature and pressure relationship existing between this specific volume of liquid sample and the carrier gas, this liquid sample immediately volatilizes upon exposure to the carrier gas. Furthermore because the sample valve 10 is connected directly to the column 12 and because of the direction of flow of the carrier gas, this liquid sample volatilizes onto the column packing directly with only minimal dead space between sample flow channel 80 and column 12 to detrimentally diffuse this sample in the carrier gas before entering the column 12. To further reduce this undesirable diffusion of the sample in the carrier gas upon the sample's volatilization in the carrier gas flowpath, it is preferred to make line 44 of smaller diameter than the diameter of column 12. In the meantime channel 82 forms a fluid path between lines 52 and 56 so that sample liquid can continue to flow through sample valve 10. This continued flow of the sample assists in maintaining the sample valve 10 in thermal equilibrium so that less time is required between sample injections.

After the carrier gas has swept the sample from carrier gas flow channel 80 on into column 12, air actuator 48 (FIG. 1) returns sample valve 10 to its first flow position as shown in FIG. 4. The timing of this return is not critical, but the sooner this valve 10 is returned to this configuration the better, for the more time the sample has to flow in sample flow channel 80, the more quickly equilibration is reached between the sample valve's temperature and the sample's temperature. More importantly, the more time the sample has to flow through sample flow channel 80, the more quickly will the walls of the sample flow channel equilibrate with the sample stream before a sample slug is again introduced into column 12 for the next test. Water absorption by the walls of the sample flow channel 80 and column 12 are major problems when measuring water in concentrations below about 100 ppm, particularly in organic streams containing HCl or chlorine.

At any rate with the sample injection valve 10 back in its first flow position along with the backflush valve 14 remaining in its first flow position or its "forward flow configuration" as shown in FIG. 4, the carrier gas sweeps the separate constituents of the sample through the column at various rates of speed, as chromatographic columns are known to do, until at least the water constituent has passed through the sample gas passageway 20 of detector 13. The detector 13 detects the amount of water present according to the directions of detector control circuit 47 (FIG. 1) and the concentration of water in the sample is recorded by recorder 50. Other devices such as an alarm could be actuated by detector control circuit when this water concentration reached a certain level if desired.

Once the water constituent is through the detector 13, it is highly desirable to immediately stop the flow of the remaining sample constituents still flowing through column 12 behind the water constituent in order to prolong the life of the column packing. This is done by starting a backflush of the column packing, as soon as possible.

Backflushing the column 12 is accomplished by no more than merely switching backflush valve 14 into its second flow position or "backflush flow configuration" as seen in FIG. 6. In this configuration the carrier gas no longer flows from line 40 through flow channel 72 of backflush valve 14 through line 44, etc. as it did when the backflush valve was in its first flow position, its "forward flow configuration". Rather, backflush valve 14 now passes the carrier gas from line 40, on through rotated flow channel 70, on through line 41, through sample gas passageway 20 of detector 13, through column 12 in the direction of from its outlet to its inlet, through carrier gas flow channel 78 of sample injection valve 10, through line 44, through flow channel 72 of backflush valve 14, and on to vent via line 42 sweeping the remaining sample constituents from the column packing of column 12. Backflush valve 14 is maintained in this second flow position or "backflush flow configuration" until these constituents are swept out of the system. The time it takes to accomplish this must be established by trial and error for each different organic stream. Once this time has elapsed backflush valve 14 is switched back into its first flow position or "forward flow configuration" as shown in FIG. 4 and the carrier gas resumes its forward flowpath as described above in the discussion of FIG. 4.

The system has now been described through one cycle of operation. This cycle is repetitively repeated automatically so that a continuous on-line monitoring of an organic process stream is achieved. It should be emphasized that all the valve switching, sample introduction, recordation of sample results, and the like are done without the necessity of having an individual perform these steps. They are all done automatically by the system. Furthermore, it should be strongly emphasized that this invention provides virtual real-time continuous monitoring. That is there is none of the delay ordinarily introduced by having to have a sample taken by an operator, to a laboratory where it must wait often its turn to be analyzed by another operator.

Having fully described the invention, what is claimed is:

1. A gas chromatographic apparatus which is capable of rapid, repetitive, on-stream process analysis comprising:
   (1) a single chromatographic column having a sample inlet and a sample outlet and containing a suitable column packing material;
   (2) a detector in direct fluid communication with the chromatographic column at the column's outlet by having the detector's sample inlet closely abutting the column's outlet;
   (3) a backflush valve which is capable of being switched to different flow positions and having at least four ports and at least two channels which are moveable with respect to these ports in a manner such that each channel is capable of forming a fluid communication link between separate pairs of the ports of the backflush valve; this backflush valve being in fluid communication via its first port with the detector through the detector's sample outlet, this backflush valve being in fluid communication via its second port with a vent, and this backflush valve being in fluid communication via its third port with a carrier gas supply source;
   (4) a sample valve which is capable of being switched to different flow positions independently of the switching of the backflush valve; said sample valve having at least four ports and at least a first, second, and third channel, the channels being moveable with respect to the sample valve's ports in a manner such that each channel is capable of forming a fluid communication link between a pair of the sample valve's four ports according to the position to which the sample valve is switched; said sample valve being in direct fluid communication via its first port with the inlet of the chromatographic column by having said inlet at least closely abutting the first port of the sample valve; said sample valve being in fluid communication via its second port with the backflush valve through the fourth port of the backflush valve; said sample valve capable of being in fluid communication via its third port with a process stream to be analyzed, and said sample valve being in fluid communication via its fourth port with an exit for the sample;
   (5) a pressure regulating means capable of maintaining carrier gas flowing into the sample valve via its second port from the fourth port of said backflush valve at a substantially lower pressure than the sample when flowing from the first port of said sample valve into the inlet of said column;
   (6) a first temperature regulating means associated with the sample valve for controlling the temperature of any sample flowing through the sample valve from a process stream to be analyzed;
   (7) a second temperature regulating means for controlling the temperature of the carrier gas, the chromatographic column, the detector and the reference cell at a predetermined, constant temperature;
   said pressure regulating means being coordinated with the first and second temperature regulating means so that liquid sample flowing in the sample valve from its third port to its fourth port through its second channel will remain liquid therein but will have sufficient energy so that it will immediately volatilize upon said sample valve's being switching to its second position wherein the sample trapped in the sample valve's second channel is suddenly injected into the carrier gas between the sample valve's first and second ports; and
   (8) a valve switching means capable of independently switching the backflush and sample valves to their different flow positions;
   said first flow position of the backflush valve being one in which one of its channels forms a fluid communication link between its first port and its second port while another of its flow channels forms a fluid communication link between its third and fourth ports;
   said second flow position of the backflush valve being one in which one of its flow channels forms a fluid communication link between its first and third ports while another of its channels forms a fluid communication link between its second and fourth ports; and
   said first flow position of the sample valve being one in which the first of its channels forms a fluid communication link between its first and second ports while its second channel forms a fluid communication link between its third and fourth ports; and
   said second flow position of the sample valve being one in which its second channel forms a fluid communication link between its first and second ports while its third channel permits a liquid communication link between its third and fourth ports.

2. The apparatus of claim 1 wherein the first port of the sample valve directly abuts the chromatographic column inlet and the chromatographic column outlet directly abuts the detector's sample inlet.

3. The apparatus of claim 1 wherein the fourth port of the sample valve is in fluid communication with the process stream from whence the sample stream was taken.

4. The apparatus of claims 1, 2 or 3 wherein said switching means are automatically operated by a programmed cyclic control unit.

* * * * *